United States Patent [19]

Olesen et al.

[11] Patent Number: Plant 5,646

[45] Date of Patent: Jan. 28, 1986

[54] ROSE PLANT

[76] Inventors: Pernille Olesen; Mogens Olesen, both of 58 Kelleriisvej, DK 3490 Kvistgaard, Denmark

[21] Appl. No.: 595,416

[22] Filed: Mar. 30, 1984

[51] Int. Cl.[4] ..... A01H 5/00

[52] U.S. Cl. ..... Plt./12

[58] Field of Search ..... Plt./12

*Primary Examiner*—Robert E. Bagwill

*Attorney, Agent, or Firm*—Vincent G. Gioia

[57] ABSTRACT

A new grandiflora rose variety of bright red and silver bicoloring and of good form.

1 Drawing Figure

The present invention relates to a new and distinct variety of rose plant of the grandiflora rose class, which was originated by crossing an unpatented, unnamed seedling of our creation as seed parent with another unpatented, unnamed seedling of our creation as pollen parent. The denomination of the new variety is "Poulart".

Among the novel characteristics possessed by this new variety which distinguish it from its parents and all other varieties of which we are aware are flowers of unusual red and silver bicoloring unique in a grandiflora rose. The flower coloring progresses from a substantially scarlet bud to flowers which when $\frac{1}{3}$ to $\frac{3}{4}$ open display a unique combination of silvery colored petal undersurfaces and red petal top surfaces, but each surface having additional color tone variations including yellow coloring at lower petal segments such as to produce an overall bright orange-red and silver bicolor effect. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society ColourChart.

Parentage: Seedling.

*Seed parent.*—Unnamed seedling.

*Pollen parent.*—Unnamed seedling.

Class: Grandiflora.

The following observations are made of specimens grown outdoors in Clackamas County, Oreg. during the month of September.

FLOWER

Blooming habit: Continuous.

A. Bud:

(1) *Size.*—Medium.

(2) *Form.*—High centered, long pointed.

(3) *Color.*—After sepals fall, scarlet, near 43C with 38D washing and silvery pink coloring on petal undersurface.

(4) *Sepals.*—Longer than bud, fancy, few glabrous hairs outside, wooly inside.

(5) *Peduncle.*—Length — Long, 4 to 6 inches. Aspect — Straight. Strength — Erect. Color — Near 53B.

B. Bloom:

(1) *Size.*—Average size when fully expanded — About $3\frac{1}{2}$ to 4 inches.

(2) *Borne.*—Several together in large sprays.

(3) *Form.*—High centered, petals reflex upon opening, stamens show at center when fully open.

(4) *Petalage.*—Number of petals under normal conditions — About 24.

(5) *Color.*—After the sepals fall revealing the undersurface of first petals, the predominant color visible is scarlet; however, the undersurface of individual petals shows this color washing through pale pink into an off-white color of silvery appearance. Upon further opening but while still in bud stage, the predominant coloring is red near 42A to B, but silvery highlights of petals' undersurfaces begin to become visible. The maximum display of the flower's bicolor is seen when blooms are $\frac{1}{3}$ to $\frac{3}{4}$ open at which time the primary color of the silvery petal undersurface, near 56D, is most visible together with the aforementioned red coloring. Even so, the undersurface of the petals also shows washing from red at the petal edges into the silvery-appearing 56D. The yellow coloring of the lower segments of the petals toward the point of petal attachment can also be seen and produces a combined orange-red general tonality from a distance. Depending upon the weather, the flowers are capable of producing what is known as a hand-painted effect on the top surfaces of the petals.

C. Petals:

(1) *Texture.*—Thick.

(2) *Appearance.*—Satiny inside and outside.

(3) *Form.*—Fan shaped, slightly wider than long, reflex as flower opens.

(4) *Arrangement.*—Regular.

(5) *Petaloids in center.*—Few.

(6) *Persistence.*—Drop off cleanly.

(7) *Fragrance.*—Slight.

(8) *Lasting quality.*—Long lasting on plant and as cut flower.

REPRODUCTIVE ORGANS

A. Stamens, filaments and anthers:
*Arrangement.*—Regularly arranged around styles.
B. Pollen:
*Color.*—Near 15A.
C. Styles: Few, longer than stamens.
D. Stigmas:
*Color.*—Near 12C.
E. Hips: Small, color near 151B, seeds do not protrude.

PLANT

A. Form: Upright.
B. Growth: Vigorous, very uniform.
*Height attained.*—About 48 inches.
C. Foliage: Compound 5 to 7 leaflets, mostly 5.
(1) *Size.*—Medium.
(2) *Quantity.*—Abundant.
(3) *Color.*—New foliage: Upper side — Near 187A. Under side — Near 187B. Old Foliage: Upper side — Near 139A. Under side — Near 138B.
(4) *Shape.*—Long oval, pointed.
(5) *Texture.*—Upper side is shiny, leathery and under side is dull.
(6) *Edge.*—Serrated.

(7) *Serration.*—Simple.
(8) *Leaf stem.*—Color — Near to 170B. Under side — Near 145A.
(9) *Stipules.*—Very long, slightly bearded.
(10) *Resistance to disease.*—Blackspot — Excellent. Mildew — Excellent. Rust — Excellent.
D. Wood:
(1) *New wood.*—Color — Near 53B. Bark — Smooth.
(2) *Old wood.*—Color — Near 137C. Bark — Smooth.
E. Thorns:
(1) *Thorns.*—Quantity (main stalk) — Few, long, narrow, nearly straight, near 44D when young. On laterals from stalk — Few.
(2) *Prickles.*—Profuse, scattered.
F. Winter hardiness: Exceptionally hardy.

We claim:

1. A new and distinct variety of rose plant of the grandiflora rose class, substantially as shown and described, characterized particularly by unique bright red and silver bicolor flowers with yellow lower petal segments producing an overall bright orange-red and silver bicolor effect.

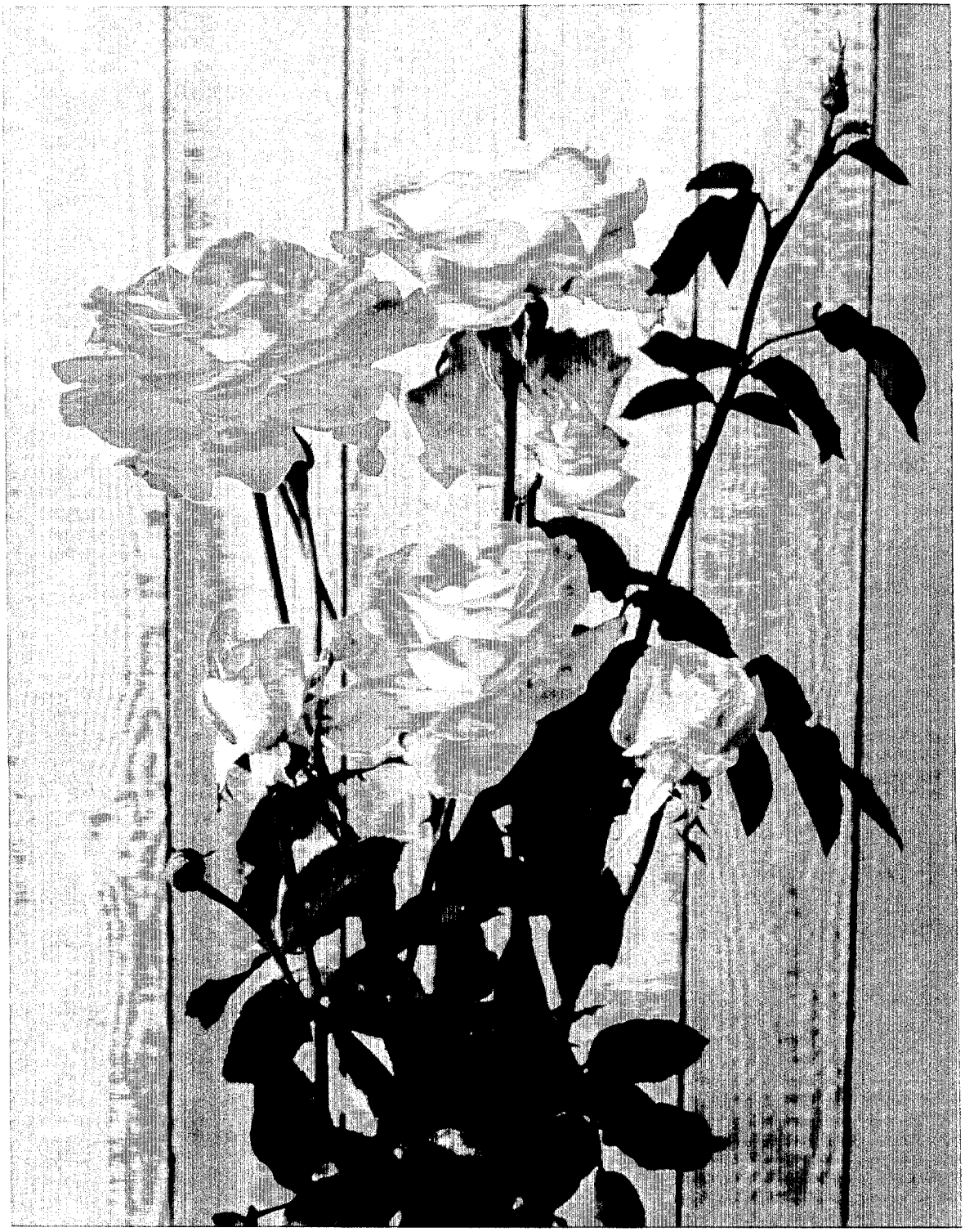

* * * * *